United States Patent [19]

Finch

[11] 4,273,779
[45] Jun. 16, 1981

[54] TREATING HYPERTENSION WITH SUBSTITUTED-5-AMINO-2-PYRIDINECARBOXYLIC ACIDS

[75] Inventor: Neville Finch, West Orange, N.J.

[73] Assignee: Ciba-Geigy Corporation, Ardsley, N.Y.

[21] Appl. No.: 842,846

[22] Filed: Oct. 17, 1977

Related U.S. Application Data

[63] Continuation-in-part of Ser. No. 753,975, Dec. 15, 1976, abandoned.

[51] Int. Cl.$^2$ ............................................. A61K 31/455
[52] U.S. Cl. ................................. 424/266; 546/289; 546/309; 546/310; 542/414
[58] Field of Search .................... 260/295 R, 294.8 G, 260/295 H, 294.9, 295 AM, 295.5 H, 295.5 A; 424/266; 546/310

[56] References Cited

U.S. PATENT DOCUMENTS

| | | | |
|---|---|---|---|
| 3,131,194 | 4/1964 | Bruce et al. | 546/325 |
| 3,454,587 | 7/1969 | Littell et al. | 546/310 |
| 3,553,203 | 1/1971 | Schwarz et al. | 260/239.1 |
| 3,663,700 | 5/1972 | Umezawa et al. | 424/266 |
| 3,712,900 | 1/1973 | Thiele et al. | 546/308 |
| 3,862,159 | 1/1975 | Umezawa et al. | 546/326 |
| 3,914,239 | 10/1975 | Kühnis et al. | 260/295 R |

OTHER PUBLICATIONS

*Chemical Abstracts,* 74: 76278v (1971) [Deady, L., et al., *Aust. J. Chem.* 1971, 24(2), 385–392].
Neunhoeffer, H., et al., *Liebigs Ann. Chem.* 761, 39–49 (1972).
*Chemical Abstracts,* 79: 91940b (1973) [Delarge, J., et al., *J. Pharm. Belg.* 1973, 28(3), 283–290].
*Chemical Abstracts,* 79: 105080k (1973) [Hidaka, H., et al., Japan Kokai 73 52,771, 7/24/73].
*Chemical Abstracts,* 84: 4816c (1976) [Noda, K., et al., Japan Kokai 75 82,075, 7/3/75].
*Chemical Abstracts,* 84: 121884j (1976) [Noda, K., et al., Japan Kokai 75 116,492, 9/11/75].

*Primary Examiner*—Alan L. Rotman
*Assistant Examiner*—Richard A. Schwartz
*Attorney, Agent, or Firm*—Norbert Gruenfeld

[57] ABSTRACT

5-Amino-2-pyridinecarboxylic acids, e.g. those of the formula

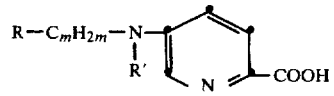

R=H, phenyl unsubst. or subst. by alkyl, alkoxy, halo, $CF_3$, Cn, $CONH_2$ or phenoxy
R'=H, alkyl or aralkyl
m=1–4 or functional derivatives thereof, are hypotensive agents.

3 Claims, No Drawings

TREATING HYPERTENSION WITH SUBSTITUTED-5-AMINO-2-PYRIDINECARBOXYLIC ACIDS

CROSS-REFERENCE TO RELATED APPLICATION

This is a continuation-in-part of application Ser. No. 753,975, filed Dec. 15, 1976 (now abandoned).

BACKGROUND OF THE INVENTION

Fusaric acid, i.e. 5-butyl-2-pyridinecarboxylic acid, the 3- and/or 6-(alkoxy, amino, halo or hydroxy)-derivatives thereof, or halofusaric amides of U.S. Pat. Nos. 3,914,239 or 3,935,221, are known antihypertensive agents, by virtue of their vasodilating and dopamine-β-hydroxylase inhibitory action, but they also produce tachycardia. Surprisingly, it was found that 2-pyridine-carboxylic acids, having a specially substituted amino group in the 5-position, instead of an alkyl, haloalkyl, alkoxy, or cycloalkoxy group therein, are not dopamine-β-hydroxylase inhibitors, and produce less tachycardia. Therefore, they are valuable hypotensive agents with minimal cardiac and other side effects.

SUMMARY OF THE INVENTION

The present invention concerns and has for its object the provision of new 5-amino-2-pyridinecarboxylic acids of the Formula I

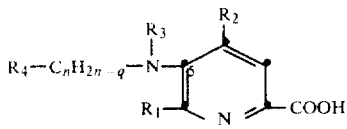

wherein each of $R_1$ and $R_2$ is hydrogen, lower alkyl or lower alkoxy, $R_3$ is hydrogen, lower alkyl, or lower aralkyl and $R_4$ is hydrogen, lower alkoxy, lower alkylthio, halogeno, amino, mono- or di-lower alkylamino, phenyl or phenyl substituted by one or more than one member selected from lower alkyl, lower alkoxy, lower alkylthio, halogeno, trifluoromethyl, cyano, carboxy or phenoxy, n is an integer from 1 to 7, q is 0 or 2, (n-q) is positive and in which 5-substituent all heteroatoms and double bonds are separated from each other by at least two carbon atoms, or a lower alkyl ester, amide, mono- or di-lower alkylamide, hydrazide or tetrazide of said acids or carboxy compounds, respectively, the N-oxide or a therapeutically useful salt thereof, as well as of corresponding pharmaceutical compositions and of methods for the preparation and application of said products, which are useful hypotensive agents which decrease collagen synthesis within the blood vessels. Said products are especially suitable for the treatment or management of hypertension in mammals.

DESCRIPTION OF THE PREFERRED EMBODIMENTS

A lower alkoxy or alkylthio group, mentioned above, is preferably methoxy or methylthio, but also ethoxy, n- or i-propoxy or -butoxy, or ethylthio. A lower alkyl or aralkyl group is preferably methyl or benzyl, but also ethyl, n- or i-propyl or -butyl, or benzyl substituted as phenyl below. A halogen atom is preferably fluoro, chloro or bromo. A mono- or di-lower alkylamino group represents preferably mono- or di(methylamino, ethylamino, n- or i-propylamino). A substituted phenyl radical $R_4$ contains preferably up to three, advantageously one or two of said members listed above, such as methyl or ethyl; methoxy or ethoxy; methylthio; fluoro, chloro or bromo; trifluoromethyl; phenoxy; or said free, esterified or amidized carboxy group present in the pyridine-2-position.

The term "lower" referred to above or hereinafter in connection with organic radicals or compounds respectively, defines such with up to 7, preferably up to 4, advantageously with one or two carbon atoms.

In the radical $R_4$—$C_nH_{2n-q}$, $R_4$ is preferably said phenyl radical, but also hydrogen or said other groups; n is preferably an integer from 1 to 4, and q is 0. Thus $C_nH_{2n-q}$ becomes preferably methylene, but also 1,1- or 1,2-ethylene, 1,1-, 1,2- or 1,3-propylene, 1,1-, 1,2-, 1,3-, 1,4- or 2,3-butylene; provided it separates heteroatoms within $R_4$, e.g. alkoxy, alkylthio or amino, from the 5-nitrogen atom by at least 2 carbon atoms. In case q is 2, said radical $C_nH_{2n-q}$ represents preferably 1,3-prop-1-enylene, 1,3-but-1-enylene or 1,4-but-1 or 2-enylene.

The N-oxide is preferably the pyridine-1-oxide of the tertiary amines, and the salts are preferably therapeutically acceptable ammonium alkali or alkaline earth metal, e.g. sodium, potassium or calcium salts of the free acids, or acid addition salts of the bases, e.g. those derived from the acids listed below.

The compounds of the invention exhibit valuable pharmacological properties, primarily hypotensive and antihypertensive activity. This is demonstrable in animal tests, using advantageously mammals, e.g. rats, cats or dogs, as test objects. The animals may either be normotensive or hypertensive, e.g. genetically or renal hypertensive rats or dogs. Said compounds can be applied to them enterally or parenterally, advantageously orally, subcutaneously, intravenously, intraperitoneally or intraduodenally, for example within gelatin capsules or in the form of starchy suspensions or aqueous solutions respectively. The applied dosage may range between about 0.1 and 200 mg/kg/day, preferably between about 1 and 100 mg/kg/day, advantageously between about 5 and 50 mg/kg/day. The lowering effect on the blood pressure is recorded either directly by means of a catheter, e.g. placed in the rat's caudal or dog's femoral artery, and a transducer, expressing the blood pressure prior and after dosing in mm/Hg, or indirectly by sphygmomanometry, e.g. at the rat's tail. Thus, for example, the 5-benzylaminopyridine-2-carboxylic acid, or the 5-(p-fluoro- or m-chlorobenzylamino)-pyridine-2-carboxylic acid, three representative members of the compounds of the invention, are very effective in said tests, some even slowing the heart rate.

Moreover, the compounds of the invention inhibit prolyl hydroxylase, which enzyme is important for collagen synthesis. In hypertensive disease there is a thickening of the major blood vessel walls due to an increase in collagen content. Thus, an increase in prolyl hydroxylase is observed in the aorta of hypertensive rats. Therefore, an inhibitor of collagen synthesis at the site of rapid turnover will be beneficial for correcting a basic problem in hypertension. Accordingly, the compounds of the invention are useful antihypertensive and the collagen synthesis reducing agents, for example in the treatment or management of essential or renal hypertension in mammals. They are also useful intermediates in the preparation of other valuable products, especially of pharmacologically active compositions.

Particularly useful are compounds of Formula I, in which each of $R_1$ and $R_2$ is hydrogen, lower alkyl or lower alkoxy, $R_3$ is hydrogen, lower alkyl or lower phenylalkyl, $R_4$ is hydrogen, lower alkoxy, lower alkylthio, halogeno, di-lower alkylamino, phenyl or phenyl substituted by up to two members selected from lower alkyl, lower alkoxy, lower alkylthio, halogen, trifluoromethyl, cyano, carboxy or phenoxy, n is an integer from 1 to 4, q is 0 or 2, (n-q) is positive, and in which 5-substituent all heteroatoms and double bonds are separated from each other by at least two carbon atoms, or a lower alkyl ester, amide, mono- or di-lower alkylamide, hydrazide or tetrazide of said acids or carboxy compounds respectively, the 1-N-oxide or a therapeutically acceptable ammonium, alkali or alkaline earth metal or acid addition salt thereof.

Outstanding compounds of the invention are those of Formula II

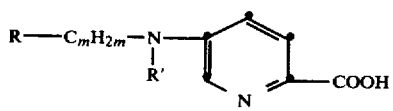

wherein R is hydrogen, phenyl, or phenyl substituted by up to two members selected from lower alkyl, lower alkoxy, halogeno, trifluoromethyl, cyano, carbamoyl or phenoxy, R' is hydrogen, lower alkyl or benzyl, m is an integer from 1 to 4, or a therapeutically acceptable ammonium, alkali metal or acid addition salt thereof.

Most preferred are the compounds of Formula II, wherein R is phenyl, tolyl, anisyl, mono- or di-(fluoro or chloro)-phenyl, bromophenyl, trifluoromethylphenyl, carbamoylphenyl or phenoxyphenyl, m is the integer 1 and R' is hydrogen, methyl, ethyl or benzyl, or a therapeutically useful ammonium, alkali metal or acid addition salt thereof.

The compounds of the invention are prepared according to methods known per se, advantageously by:

(1) hydrolyzing the nitrile of Formula III

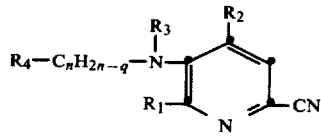

to the corresponding acid or amide, or reacting it with an alkali metal azide to form the tetrazide and, if desired, converting any resulting compound into another compound of the invention. Said hydrolysis is performed as usual, preferably with hydrogen peroxide, aqueous acids or bases, such as strong mineral or carboxylic acids, or alkali metal hydroxides respectively, e.g. hydrochloric sulfuric, perchloric or acetic acid; sodium or potassium hydroxide, advantageously in the presence of lower alkanols, e.g. methanol or ethanol. Said reaction with the azide, e.g. sodium azide, is advantageously carried out in the presence of an ammonium salt, e.g. ammonium chloride, and/or a polar solvent, such as dimethylformamide.

Another process for preparing the compounds of Formula I consists in:

(2) oxidizing the aldehyde of Formula IV

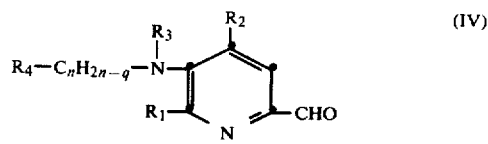

to the corresponding acid and, if desired, converting any resulting compound into another compound of the invention. Said oxidation is also performed according to standard oxidation methods, for example, with the use of mild oxidation agents, such as heavy metal oxides, e.g. silver or mercuric oxide, or according to the procedure of E. J. Corey et al, J. Am. Chem. Soc. 90, 5616 (1968). Said aldehydes are reacted with alkali metal cyanides followed by oxidation with a heavy metal oxide, preferably manganese dioxide, and hydrolysis of the resulting acyl cyanide with water or corresponding alcohols, to yield the free acids or their esters.

The compounds of the invention can also be prepared by:

(3) condensing compounds of Formulae V and VI

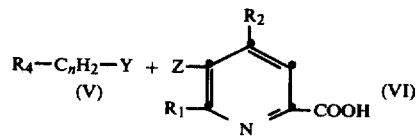

or preferably said acid derivatives of VI, wherein the group Z is a free or metallized $NHR_3$ group and Y is hydroxy esterified with a strong, inorganic or organic acid, preferably a hydrohalic, e.g. hydrochloric, -bromic or -iodic acid, or an alkane or benzene sulfonic acid, e.g. methane, ethane, benzene, p-toluene or m-bromobenzene sulfonic acid; and if desired, converting any resulting compound into another compound of the invention. Said condensation is carried out either in the presence of basic condensation agents, such as alkali metal or alkaline earth metal hydrides, hydroxides, carbonates or bicarbonates, or organic nitrogen bases, e.g. trilower alkylamines, pyridines or quinolines; or preferably with said alkali metal salts in aprotic solvents, e.g. dimethylformamide or -sulfoxide. The latter, as well as alkali metal hydrides, are advantageously employed in the condensation with $Z=NH_2$.

Another process for preparing the compounds of the invention consists in:

(4) reducing Schiff's bases or amides of Formula VII

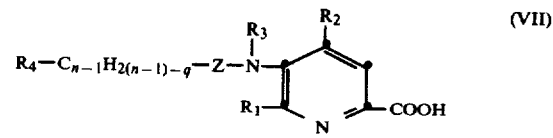

or said acid derivatives thereof, wherein Z is CHOH or CO, or $R_3+Z$ is CH and, if desired, converting any resulting compound into another compound of the invention. Said reduction is also carried out according to conventional methods. The Schiff's bases are advantageously reduced with either catalytically activated hydrogen, e.g. hydrogen in the presence of palladium, platinum or nickel catalysts, or preferably with simple or complex borohydrides, such as lower boranes or alkali metal borohydrides, especially diborane or sodium borohydride. Said amides (Z=CO) are advantageously reduced with a mixture of said boranes and borohydrides, or an agent generating both. The latter is, for example, a boron halide, e.g. boron trifluoride, reacted with an excess of said alkali metal borohydrides, e.g. sodium borohydride. Thus, one may react said amides first with about 2-50 mols of the alkali metal borohydride, advantageously at temperatures lower than room temperature, e.g. at about 0°, whereupon about 2-10 mols of borohydride, preferably in solution of a polar solvent, such as an open or cyclic aliphatic ether, e.g. diethyl ether or tetrahydrofuran, which is added at ambient temperature, e.g. between about 0° and 50°, and the excess reagent is destroyed as usual.

Finally, the compounds of the invention can be prepared by:

(5) hydrolyzing acyl derivatives of Formula VIII

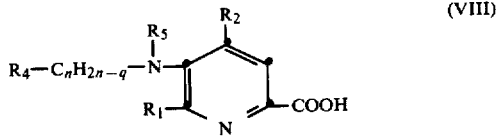

(VIII)

or said acid derivatives thereof, wherein $R_5$ is the acyl residue of an acid, preferably derived from a lower alkanoic, halogenated alkanoic, lower alkyl-carbonic or benzoic acid, e.g. acetyl, trifluoroacetyl, methoxy- or ethoxycarbonyl or benzoyl. Said hydrolysis is performed according to known methods, advantageously with aqueous bases, such as alkali metal hydroxides, e.g. sodium or potassium hydroxide, preferably in the presence of lower alkanols, e.g. methanol or ethanol.

The compounds of the invention so obtained can be converted into each other according to known methods. For example, resulting secondary amines ($R_3$=H) can be converted into tertiary amines either by reaction with lower alkyl halides or sulfonates, e.g. those mentioned under item 3), or by reductive alkylation, e.g. with formaldehyde and formic acid. Resulting free acids can be esterified with lower alkanols in the presence of said strong acids, or with diazo-lower alkanes, or converted into their halides by treatment with thionyl halides, or phosphorus halides or oxyhalides. Resulting esters may be hydrolyzed or transesterified in the presence of said alkaline or acidic agents respectively, or said esters or halides treated with ammonia, mono- or di-lower alkylamines or hydrazine, in order to obtain the amides or hydrazides. These, in turn, can be hydrolyzed or alcoholized under acidic or alkaline conditions. Resulting unsaturated compounds (q=2) can be hydrogenated, hydrohalogenated, hydrated or halogenated in known fashion and any resulting mono- or bishalide treated with alkali metal lower alkoxides or mercaptides, ammonia, mono- or di-lower alkylamines and/or alkali metal hydroxides, in order to obtain compounds with $R_4$ being lower alkoxy, lower alkylthio, amino, mono- or di-lower alkylamino. Furthermore, said compounds of Formula I can be N-oxidized, for example, with ozone, hydrogen peroxide, inorganic or preferably organic peracids, such as persulfuric, lower alkanoic or benzoic peracids, e.g. peracetic or perbenzoic acid; or resulting N-oxides reduced, either with catalytically activated hydrogen or phosphorus halides.

Finally, a resulting acid can be converted into its salts according to conventional methods, for example, by reacting it with a stoichiometric amount of a suitable salt-forming reagent, such as ammonia or an alkali or alkaline earth metal hydroxide, carbonate or hydrogen carbonate. A salt of this type can be reconverted into the free acid by treatment with an acid, e.g. hydrochloric, sulfuric or acetic acid, until the proper pH has been reached. A resulting basic compound can be converted into a corresponding acid addition salt, for example, by reacting it with an inorganic or organic acid, preferably a therapeutically useful acid, or with a corresponding anion exchange preparation, and isolating the desired salt. An acid addition salt may be converted into the free compound by treatment with a base, e.g. a metal hydroxide, ammonia or a hydroxylion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicylic, pamoic, nicotinic, methanesulfonic, ethanesulfonic, hydroxyethanesulfonic, ethylenesulfonic, benzenefulfonic, halobenzenesulfonic, toluenesulfonic, naphthalenesulfonic, sulfanilic or cyclohexylsulfamic acid.

These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

Resulting mixtures of isomers can be separated into the single isomers by methods in themselves known, e.g. by fractional distillation, crystallization and/or chromatography. Racemic products can likewise be resolved into the optical antipodes, for example, by separation of diastereomeric salts thereof, e.g. by the fractional crystallization of d- or l-camphor sulfonates or d-α-(1-naphthyl)-ethylamine or 1-cinchonidine salts.

The above reactions are carried out according to standard methods, in the presence or absence of diluents, preferably such as are inert to the reagents and are solvents thereof, of catalysts, condensing or neutralizing agents and/or inert atmospheres, at low temperatures, room temperature or elevated temperatures, at atmospheric or superatmospheric pressure.

The invention also comprises any modification of the above process, wherein a compound resulting as an intermediate at any stage thereof, is used as starting material and the remaining steps are carried out, or the process is discontinued at any stage thereof, or in which the starting material is formed under the reaction conditions or is used in the form of its salts or reactive derivatives. For example, in the above-described oxidation methods, the aldehydes IV are formed intermediarily from the corresponding 2-carbinols under the applied conditions. In the process of the invention, those starting materials are advantageously selected, which yield the above-described preferred embodiments thereof, especially those corresponding to Formula II.

The starting material used is known or, if new, may be prepared according to methods described for known analogs thereof and those illustrated by the examples herein. Thus, for example, the 5-aminopyridine-2-carboxylic acids VI and functional derivatives thereof are described in H-S Zeitschr. f. Physiol. Chem. 288, 237(1951); Pharm. Acta Helv. 44, 637(1969); Aust. J. Chem. 24, 385(1971); J. Chem. Soc. [C], 3257(1971) or J. Med. Chem. 17 No. 10, 1065(1974). They may be reacted with a limited amount of a lower alkyl or aralkyl halide or sulfonate to form the secondary amines of Formula VI.

The aldehydes IV are obtained from 5-nitro-2-methylpyridines, which are oxidized with hydrogen peroxide to give the corresponding N-oxide. The latter is rearranged with acetic anhydride and aqueous hydrochloric acid to the corresponding 2-carbinol, which is esterified, reduced, N-substituted according to items (3) or (4), hydrolyzed and oxidized with potassium permanganate or manganese dioxide to the desired aldehyde IV. It can be converted into the corresponding oxime, the latter is N-acylated, if desired, and dehydrated with methanesulfonyl chloride or acetic anhydride, followed by hydrolysis according to item (5), to yield the nitriles III.

Most of the starting materials V are commercially available as, for example, lower alkyl, aralkyl or allyl halides, especially bromides and various other reactive esters, and the preparation of compounds VII requires corresponding aldehydes and said 5-aminopyridine-2-carboxylic acids VI, or said derivatives thereof. Finally, the acyl derivatives VIII are obtained analogous to item (3) by condensing compounds VI, wherein Z is a free or metallized $NHR_5$ group, with compounds V.

The pharmacologically active compounds of the invention are useful in the manufacture of pharmaceutical compositions comprising an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) absorbents, colorants, flavors and sweeteners. Injectable compositions are preferably aqueous isotonic solutions or suspensions, and suppositories are advantageously fatty emulsions or suspensions. They may be sterilized and/or contain adjuvants, such as preserving, stabilizing, wetting or emulsifying agents, solution promotors, salts for regulating the osmotic pressure and/or buffers. They may also contain other therapeutically valuable substances. Said pharmaceutical compositions are prepared according to conventional mixing, granulating or coating methods respectively and contain about 0.1 to 75%, preferably about 1 to 50% of the active ingredient.

The following examples, illustrating the invention, are not to be construed as being limitations thereon. Temperatures are given in degrees Centigrade, all parts wherever given are parts by weight and, if not otherwise stated, all evaporations are carried out under reduced pressure, e.g. between about 0.1 and 15 mmHg.

EXAMPLE 1

To the stirred mixture of 8 g of sodium borohydride and 350 ml of methanol, cooled to −2°, the solution of 20 g of 5-(m-chlorobenzylideneamino)-pyridine-2-carboxylic acid methyl ester in 60 ml of dimethylformamide sufficiently warm for dissolution is added all at once and the container of the latter is washed with 15 ml dimethylformamide and 20 ml methanol containing 0.5 g of sodium borohydride. The mixture warms to about 20°, is cooled to 0° for 40 minutes and stirred at 25° for 15 minutes. It is cooled again to 0° and 9 ml of 12 N hydrochloric acid, 2 ml of acetic acid and 200 ml of ice water are added in this order. The resulting solution is diluted with crushed ice to about 1,000 ml, extracted with ethyl acetate and diethyl ether, the extract dried and evaporated. The residue is first recrystallized from diethyl ether/hexane and then from ethyl acetate/diethyl ether, to yield the 5-(m-chlorobenzylamino)-pyridine-2-carboxylic acid methyl ester of the formula

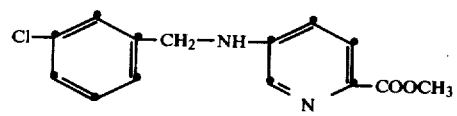

melting at 111°-113°.

The starting material is prepared as follows: The mixture of 30.44 g of 5-aminopyridine-2-carboxylic acid methyl ester, 30.9 g of m-chlorobenzaldehyde and 400 ml of benzene is refluxed on a water-trap for 3 days. It is evaporated and the residue recrystallized from benzene/ethylacetate/diethyl ether, to yield the 5-(m-chlorobenzylideneamino)-pyridine-2-carboxylic acid methyl ester melting at 139°-142°.

EXAMPLE 2

The mixture of 10 g of 5-(m-chlorobenzylamino)-pyridine-2-carboxylic acid methyl ester, 13 ml of 35% aqueous formaldehyde and 13 ml of formic acid is stirred at the steam bath for one day. It is evaporated, the residue boiled with 100 ml of methanol, until dissolution, the solution filtered hot and the filtrate cooled. The precipitate formed is collected and recrystallized from methanol, to yield the 5-(N-methyl-N-m-chlorobenzylamino)-pyridine-2-carboxylic acid melting at 138°-140°.

EXAMPLE 3

To the solution of 7 g of 5-(m-chlorobenzylamino)-pyridine-2-carboxylic acid methyl ester in 30 ml of isopropanol, 15 ml of 2 N aqueous sodium hydroxide are added and the mixture is warmed on the steam bath for ½ hour. It is diluted with 20 ml of isopropanol and 20 ml of diethyl ether whereupon a precipitate formes on cooling. It is collected and recrystallized from the mixture of 15 ml of water and 5 ml of isopropanol, to yield the sodium 5-(m-chlorobenzylamino)-pyridine-2-carboxylate melting at 250°-255°.

EXAMPLE 4

To the stirred solution of 8 g of sodim borohydride in 300 ml of methanol the solution of 15 g of 5-cinnamylideneaminopyridine-2-carboxylic acid methyl ester in 60 ml of warm dimethylformamide is added during ½ hour while cooling with ice. Simultaneously a 5 g portion and a 3 g portion of sodium borohydride is added and the mixture stirred for 1 hour at 0°. It is warmed to about 20° until dissolution occurs and combined with 18 ml of 12 N hydrochloric acid, 5 ml of acetic acid and 600 ml of ice water. The mixture is cooled to −10°, filtered, the residue washed with water, dried and recrystallized from aqueous methanol, to yield the 5-cinnamylamino-pyridine-2-carboxylic acid methyl ester melting at 131°–133°.

The starting material is prepared as follows: The mixture of 7.61 g of 5-amino-pyridine-2-carboxylic acid methyl ester, 7.61 g of trans-cinnamaldehyde and 130 ml of benzene is stirred and refluxed on a water trap for 4½ hours. It is evaporated and the residue recrystallized from ethyl acetate, to yield the 5-cinnamylideneaminopyridine-2-carboxylic acid methyl ester melting at 128°–131°.

EXAMPLE 5

To the solution of 11.9 g of 5-cinnamylamino-pyridine-2-carboxylic acid methyl ester in 25 ml of isopropanol, 28 ml of 2 N aqueous sodium hydroxide are added and the mixture intermittently heated on the steam bath for 40 minutes. It is cooled, decolorized with charcoal, filtered and the filtrate slightly acidified with hydrochloric acid and acetic acid. The mixture is extracted with benzene, the extract dried, evaporated and the residue recrystallized from benzene/methanol, to yield the 5-cinnamylaminopyridine-2-carboxylic acid melting at 178°–183°.

EXAMPLE 6

The solution of 24.9 g of 5-benzylideneaminopyridine-2-carboxylic acid methyl ester in 70 ml of hot dimethylformamide is added all at once to the solution of 7.0 g of sodium borohydride in 300 ml of methanol while stirring at −20° C. The temperature of the reaction mixture raises spontaneously to 20° and is lowered to 0° by cooling. After 2 hours the mixture is warmed to room temperature for 15 minutes to ensure complete reaction. Approximately ½ of the methanol is distilled off, the concentrate is cooled to 0° and 3 ml of acetic acid and the solution of 12 ml of 12 N hydrochloric acid in 100 ml ice water is added. A precipitate begins to separate and 200 ml more ice water are added. After 30 minutes the precipitate is collected and washed well with water and recrystallized from acetonitrile, to yield the 5-benzylaminopyridine-2-carboxylic acid methyl ester, melting at 104°–107°.

The mixture of 6 g thereof, 25 ml of 1 N aqueous sodium hydroxide and 8 ml of methanol is stirred for one hour at room temperature. The resulting solution is filtered and its pH is adjusted to 4 with 12 N hydrochloric acid. A precipitate separates, which is collected by filtration and recrystallized from acetonitrile, to yield the corresponding acid melting at 158°–164°.

The starting material is prepared as follows: The mixture of 17.4 g of 5-aminopyridine-2-carboxylic acid methyl ester, 14.0 g of benzaldehyde and 100 ml of benzene is stirred and refluxed on a water separator for 6.5 hours. The resulting clear solution is evaporated, and the residue recrystallized from benzene-hexane first, then from acetonitrile-diethyl ether, to yield the 5-benzylideneaminopyridine-2-carboxylic acid methyl ester, melting at 84°–89°.

EXAMPLE 7

The mixture of 4.84 g of 5-benzylaminopyridine-2-carboxylic acid methyl ester, 8 ml of 97% aqueous formic acid and 8 ml of 37% aqueous formaldehyde is heated on a steam bath for 22 hours. It is evaporated, the residue dissolved in water and the solution again evaporated. A third such cycle with acetonitrile-toluene yields a solid which is recrystallized from 90% aqueous acetonitrile, to yield the 5-(N-methyl-N-benzylamino)-pyridine-2-carboxylic acid melting at 168°–173°.

EXAMPLE 8

The solution of 18.6 g of 5-(m-fluorobenzylideneamino)-pyridine-2-carboxylic acid methyl ester in 50 ml of hot dimethylformamide is added all at once to the solution of 5.0 g of sodium borohydride in 230 ml of methanol at −20° while stirring. The mixture warms to approximately 0° and after one hour the mixture is warmed to 35° for 10–15 minutes. It is cooled, one-half of the methanol is distilled off and the cold concentrate is conbined with 2 ml of acetic acid and the solution of 9 ml of 12 N hydrochloric acid in 70 ml of ice water. The clear solution, (pH=6) is cooled and stirred while additional ice and water is added to cause the solution to become faintly cloudy. The precipitate is collected and recrystallized from aqueous methanol, to yield the 5-(m-fluorobenzylamino)-pyridine-2-carboxylic acid methyl ester melting at 89°–92°.

The suspension of 4 g thereof in 15 ml of 1 N aqueous sodium hydroxide is stirred at room temperature for one hour, yielding a clear solution. The pH thereof is adjusted to 8 with hydrochloric acid, charcoal is added and the mixture filtered. The clear filtrate is acidified with 12 N hydrochloric acid to pH=4, the precipitate formed is collected by filtration and recrystallized from aqueous acetonitrile, to yield the corresponding acid melting at 164°–167°.

The starting material is prepared as follows: The mixture of 11.25 g of 5-aminopyridine-2-carboxylic acid methyl ester, 10.0 g of m-fluorobenzaldehyde and 50 ml of benzene is refluxed for 22 hours on a water trap. It is evaporated and the residue recrystallized from acetonitrile, to yield the 5-(m-fluorobenzylideneamino)-pyridine-2-carboxylic acid methyl ester, melting at 111°–114°.

EXAMPLE 9

The solution of 13.7 g of 5-(3,4-dichlorobenzylideneamino)-pyridine-2-carboxylic acid methyl ester in 35 ml of hot dimethylformamide is added all at once to the solution of 3.25 g of sodium borohydride in 150 ml of methanol while stirring at −20°. The mixture warms to 10° and the temperature is lowered by application of a bath to 0°. After one hour the reaction mixture is warmed to 35° for 10 minutes, cooled again to 0° and 1.5 ml of acetic acid and the solution of 6 ml 12 N hydrochloric acid in 45 ml of ice water is added. A solid separates, more ice and water are added to complete crystallization. The solid is collected, washed with cold water and recrystallized from methanol, to yield the 5-(3,4-dichlorobenzylamino)-pyridine-2-carboxylic acid methyl ester melting at 158°–161°.

The starting material is prepared as follows: The mixture of 7 g of 5-aminopyridine-2-carboxylic acid methyl ester, 8.9 g of 3,4-dichlorobenzaldehyde, and 40 ml benzene are refluxed for 29 hours on a water-separating trap. The initial suspension becomes a clear solution, which is evaporated. The solid residue is triturated with diethyl ether and recrystallized from acetonitrile, to yield the 5-(3,4-dichlorobenzylideneamino)-pyridine-2-carboxylic acid methyl ester melting at 202°–207°.

EXAMPLE 10

The mixture of 13 g of 5-(3,4-dichlorobenzylamino)-pyridine-2-carboxylic acid methyl ester, 18 ml of formic acid and 18 ml of 37% aqueous formaldehyde is heated for 18 hours on a steam bath. It is evaporated, water is added and the mixture again evaporated. A third such process with toluene gives a yellow solid which is dissolved in a small volume of methanol and added to 53 ml of 1 N aqueous sodium hydroxide. The mixture is stirred 2 hours at ambient temperature then the pH is adjusted to 8 with hydrochloric acid. The solution is filtered and the pH is adjusted to 4 by addition of 12 N hydrochloric acid. The precipitate is collected and recrystallized from acetic acid-ethanol (1:1), to yield the 5-(N-methyl-N-3,4-dichlorobenzylamino)-pyridine-2-carboxylic acid melting at 193°–197°.

EXAMPLE 11

4.93 g of 5-(m-chlorobenzylamino)-pyridine-2-carboxaldehyde are added in small portions to the cold stirring solution consisting of 70.4 g of silver nitrate in 150 ml of water and 33.1 g of sodium hydroxide in 150 ml of water. The mixture is stirred 10 minutes after the last of the aldehyde is added and filtered. The yellow filtrate is cooled and 12 N hydrochloric acid is added until the pH is 5. A solid precipitates which is collected by filtration and crystallized from methanol, to yield the 5-(m-chlorobenzylamino)-pyridine-2-carboxylic acid melting at 170°–174°.

The starting material is prepared as follows: the mixture of 30.44 g of 5-aminopyridine-2-carboxylic acid methyl ester, 30.9 g of m-chlorobenzaldehyde, and 400 ml of benzene is refluxed for 3 days on a water-separating trap. The initial suspension eventually becomes a pale yellow solution, which is evaporated. The residual yellow solid is recrystallized from benzene-ethyl acetate-diethyl ether, to yield the 5-(m-chlorobenzylideneamino)-pyridine-2-carboxylic acid methyl ester melting at 139°–142°.

The solution of 217.5 g thereof in 880 ml of hot dimethylformamide is added all at once to the stirred solution of 100 g of sodium borohydride in 3,000 ml of methanol at −25°. The temperature of the mixture rises to 5° C., and slowly returns to −10° while cooling. After 30 minutes since the beginning of the reaction, the mixture is warmed to 25° for 1.5 hours to ensure complete reaction. Approximately 2,000 ml of the methanol are evaporated, the remaining mixture is cooled and 30 ml of acetic acid and 175 ml of 12 N hydrochloric acid diluted to 1,000 ml with ice water are added. The mixture is now cloudy and an additional 5,000 ml of ice water are added with stirring. The precipitate is collected after cooling to −10°, to yield the 5-(m-chlorobenzylamino)-pyridine-2-carboxylic acid methyl ester, which is identical with the product obtained according to Example 1.

The filtrate is extracted with two 500 ml portions of methylene chloride, the extract is washed 2 times with water, dried and evaporated. The residual yellow oil is crystallized from aqueous methanol to give a gummy crystalline solid, which is triturated with diethyl ether-hexane and the resulting cream colored powder is recrystallized from ethyl acetate-diethyl ether (2:3), to yield the 5-(m-chlorobenzylamino)-pyridine-2-carbinol melting at 85°–88°.

The mixture of 2.48 g thereof, 8 g of manganese dioxide and 100 ml of chloroform is refluxed for 2 hours, filtered and evaporated. The residue is dissolved in ethyl acetate, the solution washed with saturated aqueous sodium bicarbonate and water, dried and evaporated. The residue is recrystallized from ethyl acetate-diethyl ether, to yield the 5-(m-chlorobenzylamino)-pyridine-2-carboxaldehyde melting at 102°–105°.

EXAMPLE 12

The mixture of 5.0 g of 5-(N-methyl-N-m-chlorobenzylamino)-pyridine-2-carboxylic acid, 50 ml of thionyl chloride and two drops of dimethylformamide is refluxed for 2.5 hours. It is evaporated, the residue dissolved in 100 ml of tetrahydrofuran and added slowly to 100 ml of cold tetrahydrofuran which is saturated with ammonia. The solution is stirred for ½ hour and the excess ammonia removed by heating on a steam bath. The remaining solution is cooled and ice water is added until the volume is 500 ml, whereupon a solid precipitates, which is collected and recrystallized from methanol, to yield the 5-(N-methyl-N-m-chlorobenzylamino)-pyridine-2-carboxylic acid amide, melting at 178°–183°.

EXAMPLE 13

The suspension of 5.2 g of 5-(N-carbethoxy-N-m-trifluoromethylbenzylamino)-pyridine-2-carboxylic acid ethyl ester, 25 ml of 20% aqueous potassium hydroxide and 15 ml of ethanol is refluxed for 4 hours, whereupon the ethanol is removed by distillation and the aqueous mixture is refluxed for 28 hours longer. The resulting solution is cooled, diluted to 75 ml with water and acidified with concentrated hydrochloric acid. The solid precipitate is collected, redissolved in 10% aqueous potassium bicarbonate and the solution washed with methylene chloride. The aqueous solution is mixed with charcoal, filtered and the filtrate acidified with 12 N hydrochloric acid, to yield the 5-(m-trifluoromethylbenzylamino)-pyridine-2-carboxylic acid melting at 216°–217°.

The starting material is prepared as follows: The suspension of 10 g of 6-carbethoxynicotinic acid in 40 ml of thionyl chloride is refluxed for 2 hours and evaporated. The residue is suspended in toluene and the mixture again taken to dryness. Another such cycle is repeated to yield the pure 6-carbethoxynicotinoyl chloride. It is dissolved in 150 ml of acetone and the solution cooled in an ice bath to 10°. 4.2 g of sodium azide, dissolved in 20 ml of water, are added dropwise to the acetone solution, whereupon a solid separates after several minutes. The mixture is stirred for 2 hours in the ice bath, then 150 ml of ice water are added and the solid is collected and washed with ice water, to yield the 6-carbethoxynicotinoyl azide.

The suspension of 10 g thereof in 200 ml of toluene is slowly heated to reflux and the resulting solution refluxed for 2 hours. Then 50 ml of ethanol are added dropwise and the mixture is refluxed for an additional 2 hours. It is evaporated and the tan solid recrystallized from ethanol to yield the 5-carbethoxyaminopyridine-2-carboxylic acid ethyl ester melting at 177°–178°.

The solution of 5.9 g thereof in 50 ml of dimethylformamide is added dropwise to the suspension of 0.9 g of sodium hydride in 20 ml of dimethylformamide. Gas evolution is immediate and ceases after several minutes. The solution is stirred for 15 minutes and 5.8 g of m-trifluoromethylbenzyl chloride, dissolved in 20 ml of dimethylformamide, are added dropwise. The mixture is then warmed to 60° for 16 hours, evaporated and the residual red oil is taken up in methylene chloride. The solution is washed with 2 N hydrochloric acid and water, dried and evaporated, to give the oily 5-(N-carbethoxy-N-m-trifluoromethylbenzylamino)-pyridine-2-carboxylic acid ethyl ester.

EXAMPLE 14

To the solution of 1.38 g of 5-(m-chlorobenzylamino)-pyridine-2-carboxylic acid methyl ester in 15 ml of dimethylformamide, 0.12 g of sodium hydride in 2 ml of dimethylformamide are added and the mixture is stirred several minutes. Then 0.97 g of m-chlorobenzyl chloride are added and the mixture is stirred at room temperature for 18 hours. It is made acidic with diluted hydrochloric acid and extracted with diethyl ether. The extract is washed with 10% aqueous potassium bicarbonate and water, dried and evaporated, to yield the 5-[di-(m-chlorobenzyl)-amino]-pyridine-2-carboxylic acid methyl ester.

2 g thereof are dissolved in 10 ml of methanol containing 2 ml of 2 N aqueous sodium hydroxide. The solution is stirred 16 hours at room temperature and then diluted with 10 ml of water. It is washed with diethyl ether, the aqueous phase acidified with 2 N hydrochloric acid and extracted with diethyl ether. The extract is washed with water, dried, evaporated, and the residue crystallized from diethyl ether-methanol (5:1) to yield the corresponding free acid melting at 108°–110°.

EXAMPLE 15

The mixture of 811 g of 5-(N-carbomethoxy-N-p-fluorobenzylamino)-pyridine-2-carboxylic acid methyl ester and 5,000 ml of 20% aqueous potassium hydroxide is refluxed for 5 hours while stirring under nitrogen. The solution is diluted with 12,000 ml of water, filtered and the filtrate acidified with 1,200 ml of 38% hydrochloric acid to pH=3.5 while cooling and stirring for an hour. The precipitate is collected, washed 4 times with a total of 2,000 ml of water and dried at 70° and 3 mm Hg. 1,351 g thereof are dissolved in 16,000 ml of boiling dioxane, the solution filtered, the filtrate concentrated to about 7,000 ml at 10 mm Hg and allowed to cool to room temperature while stirring. The crystals formed are collected and 1,046 g thereof dissolved in 5,000 ml of glacial acetic acid at 95%. The solution is allowed to stand overnight at room temperature, the precipitate collected and washed with 500 ml of glacial acetic acid, followed by 1,000 ml of diethyl ether, to yield the 5-(p-fluorobenzylamino)-pyridine-2-carboxylic acid acetate.

1,200 g thereof are dissolved in 25,000 ml of 0.3 N aqueous sodium hydroxide and the solution is carefully acidified with about 660 ml of concentrated hydrochloric acid to pH=3.5 while stirring and cooling. The precipitate formed is collected and washed 10 times with a total of 2,000 ml of water, to yield the corresponding free acid melting at 197°–200°.

The starting material is prepared as follows: The suspension of 3,000 g at 6-carboxy-nicotinic acid in 18,000 ml of methanol and 300 ml of concentrated sulfuric acid is refluxed for 3 hours while stirring under nitrogen. The solution formed is cooled to 5°, diluted with 18,000 ml of water, the resulting suspension stirred for 1 hour at 5°, the precipitate collected and washed with 4,000 ml of water, to yield the 6-carbomethoxynicotinic acid melting at 195°–202°.

The mixture of 1,027 g thereof and 1,500 ml of thionyl chloride is refluxed for 2 hours and the resulting solution evaporated at 10 mm Hg. The residue is taken up three times in 2,000 ml of toluene and the mixture evaporated each time, to yield the 6-carbomethoxy-nicotinoyl chloride.

It is dissolved in 14,000 ml of acetone at 45°, the solution filtered and the filtrate added during 2 hours to the solution of 450 g of sodium azide in 14,000 ml of water while stirring at 5°–10° under nitrogen. After another hour, the resulting suspension is filtered, the residue washed 12 times with a total of 1,000 ml of water and dried at room temperature at 3 mm Hg, to yield the 6-carbomethoxy-nicotinoyl azide melting at 124°–126°.

696 g thereof are added portionwise during 45 minutes to 6,400 ml of refluxing toluene while stirring under nitrogen. The suspension is allowed to cool to 40° and 475 ml of methanol are added during 30 minutes. The mixture is stirred at 50° for another 30 minutes and overnight at room temperature. It is filtered and the residue washed with 2,500 ml of toluene, to yield the 5-methoxycarbonylamino-pyridine-2-carboxylic acid methyl ester melting at 211°–213° (analogously the n-propyl ester is obtained, m.p. 150°–152°).

To the suspension of 525 g thereof in 4,000 ml of dimethylsulfoxide 130 g of 50% sodium hydride in mineral oil are added while stirring under nitrogen for 2 hours at 38°. The resulting solution is warmed to 60° and 400 g of p-fluorobenzylchloride are added during 30 minutes, whereupon the mixture is stirred for 16 hours at 60°–70° and allowed to cool to room temperature. It is poured into 20,000 ml of stirred ice water, the dried and evaporated, to yield the 5-(N-carbomethoxy-N-p-fluorobenzylamino)-pyridine-2-carboxylic acid methyl ester as a viscous oil.

EXAMPLE 16

50 g of 5-(p-fluorobenzylamino)-pyridine-2-carboxylic acid are suspended in 700 ml of methanol and the solution saturated with gaseous hydrogen chloride. The saturated solution is refluxed for 3½ hours and most of the methanol is removed under reduced pressure. The concentrate is poured into ice water and the mixture neutralized with sodium bicarbonate. It is extracted with ethyl acetate-diethyl ether (1:1), the organic phase washed with water, dried and evaporated. The residue is crystallized from ethyl acetate-diethyl ether (1:5), to yield the 5-(p-fluorobenzylamino)-pyridine-2-carboxylic acid methyl ester melting at 107°–108.5°.

EXAMPLE 17

3.0 g of 50% sodium hydride in mineral oil are washed 2 times with hexane and suspended in 50 ml of dimethylsulfoxide. 4.5 g of formamide are added and the mixture is stirred until the gas evolution ceases. 13 g of 5-(p-fluorobenzylamino)-pyridine-2-carboxylic acid methyl ester in 50 ml of dimethylsulfoxide are then added, the mixture stirred 10 minutes and warmed on a steam bath for 5 minutes. It is stirred at room temperature for 1½ hours, 5 ml of acetic acid are added and the volume made up with water to 700 ml. The solution is then basified with saturated aqueous sodium carbonate, the precipitate collected and crystallized from isopropanol, to yield the 5-(p-fluorobenzylamino)-pyridine-2-carboxamide melting at 160°–164°.

EXAMPLE 18

1.38 g of ethylamine are dissolved in 10 ml of tetrahydrofuran at −25° under nitrogen, followed by the dropwise addition of 10 ml of 1.6 N n-butyl lithium in tetrahydrofuran. The solution is stirred 20 minutes at −25°, whereupon the solution of 3.9 g of 5-(p-fluorobenzylamino)-pyridine-2-carboxylic acid methyl ester in 20 ml of tetrahydrofuran is added dropwise, while the temperature is maintained at −20°. The mixture is allowed to warm to room temperature, then warmed to 40° and stirred an additional hour at room temperature. It is diluted with water, extracted with diethyl ether, the extract washed with water, dried and evaporated. The residue is crystallized from ethyl acetate, to yield the 5-(p-fluorobenzylamino)-pyridine-2-N-ethylcarboxamide melting at 123°–126°.

EXAMPLE 19

2.7 g of dimethylamine are dissolved in 20 ml of tetrahydrofuran at −45°, followed by the dropwise addition of 20 ml of 1.6 N n-butyl lithium in tetrahydrofuran. The mixture is stirred 20 minutes at −30°, then the solution of 7.8 g of 5-(p-fluorobenzylamino)-pyridine-2-carboxylic acid methyl ester in 40 ml of tetrahydrofuran is added dropwise at or below −25°. The mixture is then warmed to room temperature, stirred for one hour and diluted with 40 ml of water. It is extracted with diethyl ether, the organic phase washed with water, dried and evaporated, to give an oil which solidifies on standing. Acidification of the aqueous phase to pH=3 and re-extraction gives an additional crop. The combined residues are crystallized from ethyl acetate, to yield the 5-(p-fluorobenzylamino)-pyridine-2-dimethylcarboxamide melting at 136°–138°.

EXAMPLE 20

To the stirred suspension of 0.23 g of 5-(p-fluoro-benzylamino)-pyridine-2-carboxylic acid nitrile, 0.5 ml of ethanol and 0.38 g of 30% aqueous hydrogen peroxide, 0.126 g of 10% aqueous sodium hydroxide are added. The solids dissolve first, whereupon a precipitate appears. The mixture is stirred for 3 hours at 50° and diluted with water. It is filtered and the residue washed with ethanol, to yield the 5-(p-fluorobenzylamino)-pyridine-2-carboxamide melting at 166°–169°.

EXAMPLE 21

0.227 g of 5-(p-fluorobenzylamino)-pyridine-2-carboxylic acid nitrile are dissolved in 2.5 ml of warm n-propanol, the solution combined with 2.5 ml of 20% aqueous potassium hydroxide and warmed on the steam bath for 16 hours. It is diluted with water, the n-propanol removed with a stream of air, the solution cooled and acidified to pH=9 with hydrochloric acid. It is filtered and the pH of the filtrate adjusted to 4. A solid formed is collected and air-dried, to yield the 5-(p-fluorobenzylamino)-pyridine-2-carboxylic acid melting at 195°–197.5°.

EXAMPLE 22

0.245 g of 5-(p-fluorobenzylamino)-pyridine-2-carboxamide are dissolved in 2.5 ml of warm n-propanol, the solution is combined with 2.5 ml of 20% aqueous potassium hydroxide and the mixture is heated on a steam bath for 16 hours. It is diluted with water and most of the n-propanol removed with a stream of nitrogen. The hot solution is filtered and the pH of the filtrate adjusted to 4 with hydrochloric acid. The precipitate formed is collected, redissolved in aqueous sodium bicarbonate, the solution filtered and reacidified with hydrochloric acid to pH=4. The solid formed is collected and air-dried, to yield the 5-(p-fluorobenzylamino)-pyridine-2-carboxylic acid melting at 196°–198°.

EXAMPLE 23

0.5 g of 5-(p-fluorobenzylamino)-pyridine-2-carboxylic acid are dissolved in 5 ml of warm acetic acid and dry hydrogen chloride is added until the solution is saturated. Thereupon, nitrogen is bubbled into the solution for several minutes, the solid formed is collected and washed with diethyl ether to yield the 5-(p-fluorobenzylamino)-pyridine-2-carboxylic acid hydrochloride melting at 248°–253° with decomposition.

EXAMPLE 24

5.77 g of 5-(p-fluorobenzylamino)-pyridine-2-carboxylic acid are dissolved in 40 ml of water and 20 ml of 2 N aqueous sodium hydroxide. The solution is stirred at room temperature and 3.6 g of 40% aqueous peracetic acid are added. The solution becomes green and within less than a minute a solid separates. Another 3.6 g of said peracetic acid are added and the mixture is stirred for 4 hours. The pH of the mixture is adjusted to 4 with hydrochloric acid and filtered after cooling. The solid is collected and recrystallized from 90% aqueous acetonitrile, to yield the 5-(p-fluorobenzylamino)-pyridine-2-carboxylic acid N-oxide melting at 206°–209°.

3 g thereof are suspended in 10 ml of ethanol while stirring, and the mixture of 2 ml of 10 N aqueous sodium hydroxide and 18 ml of ethanol is added slowly, followed by 3 ml of water and 20 ml of ethanol while cooling. The solid formed is collected and recrystallized from aqueous ethanol, to yield the sodium salt of the 5-(p-flurobenzylamino)-pyridine-2-carboxylic acid N-oxide melting at 185°–230° with decomposition.

EXAMPLE 25

3 g of 5-cinnamylamino pyridine-2-carboxylic acid are dissolved in 50 ml of 0.5 N aqueous sodium hydroxide containing 1 ml of ethanol and the solution is hydrogenated over 0.5 g of 10% palladium on charcoal at atmospheric pressure and room temperature. After the hydrogen uptake has ceased, the mixture is filtered and the filtrate acidified with hydrochloric acid. The solution is extracted with ethyl acetate, the extract washed with water, dried, evaporated and the residue crystallized from methanol, to yield the 5-(3-phenylpropylamino)-pyridine-2-carboxylic acid melting at 167°–169°.

EXAMPLE 26

4.62 g of 5-(p-fluorobenzylamino)-pyridine-2-carboxaldehyde are added in small portions to the cold stirring mixture consisting of 70.4 g of silver nitrate in 150 ml of water and 33.1 g of sodium hydroxide in 150 ml of water. The mixture is stirred 10 minutes after the last of the aldehyde is added and filtered. The filtrate is cooled, acidified with 12 N hydrochloric acid to a pH=4, filtered and the residue washed with water to yield the 5-(p-fluorobenzylamino)-pyridine-2-carboxylic acid melting at 197°–200°. The starting material is prepared as follows:

2.5 g of 5-nitro-2-picoline are dissolved in 60 ml of methylene chloride and 4.05 g (20 m mole) of 85% m-chloroperbenzoic acid are added while stirring at room temperature. Stirring is continued overnight and the mixture is washed twice with aqueous sodium bicarbonate and then with water. It is dried, evaporated and the residue crystallized from acetonitrile, to yield the 5-nitro-2-picoline-N-oxide melting at 149°–153°.

2.2 g thereof are dissolved in 15 ml of acetic anhydride and the solution is refluxed for 5 hours. It is cooled, diluted with methanol and evaporated. The residue is redissolved in warm methylene chloride, the solution filtered and the filtrate evaporated. The residue is distilled and the fraction boiling at 125°–150°/0.3 mm Hg collected, to yield the 2-acetoxymethyl-5-nitropyridine.

0.49 g thereof are dissolved in 100 ml of ethyl acetate and the solution is hydrogenated over 1 g of Raney Nickel at 2.7 atm. until the uptake of hydrogen ceases. The mixture is filtered and the filtrate evaporated, to yield the 2-acetoxymethyl-5-aminopyridine.

0.5 g thereof are dissolved in 80 ml of benzene containing 0.5 g of p-flurobenzaldehyde. The mixture is refluxed for 4 hours on a water trap, evaporated and the residue crystallized from diethyl ether, to yield the 2-acetoxymethyl-5-p-fluorobenzylideneaminopyridine melting at 83°–86°.

0.34 g thereof are dissolved in 1 ml of dimethylformamide and the solution is added all at once to 4 ml of 2.6 millimolar sodium borohydride in methanol at −20°. The mixture is stirred for 90 minutes while coming to room temperature. It is warmed to 40°, then 2 drops of glacial acetic acid are added, followed by 2 ml of 1 N hydrochloric acid. The mixture is diluted with water, extracted methylene chloride, dried and evaporated. The residue is redissolved in ethyl acetate-diethyl ether (1:1) and extracted with 1.5 N hydrochloric acid. The aqueous phase is basified, extracted with said ethyl acetate-diethyl ether, the extract washed, dried and evaporated, to yield the 2-acetoxymethyl-5-p-fluorobenzylaminopyridine showing in the IR-spectrum bands at 1725 and 3300 cm$^{-1}$.

0.3 g thereof are dissolved in the mixture of 3 ml of 1 N aqueous sodium hydroxide and 3 ml of ethanol and the whole is refluxed for 3 hours on a steam bath. The mixture is cooled, diluted with water and washed with diethyl ether. The ether extract is washed with water and the pH of the combined aqueous phases is adjusted to 8. They are extracted with methylene chloride, the extract washed with water, dried evaporated and the residue crystallized from ethyl acetate-diethyl ether, to yield the 2-hydroxymethyl-5-p-fluorobenzylaminopyridine melting at 131°–135°.

20.05 g thereof are dissolved in 900 ml of chloroform, 70 g of manganese dioxide are added and the mixture is refluxed for 2 hours. It is filtered hot and the residue washed with hot chloroform. The filtrate is evaporated and the residue crystallized rom ethyl acetate-diethyl ether, to yield the 5-(p-fluorobenzylamino)-pyridine-2-carboxaldehyde melting at 124°–126°.

Said aldehyde can also be converted to the nitrile used in Examples 21 and 22 thus: 17.0 g thereof are dissolved in the mixture of 80 ml of ethanol and 80 ml of pyridine. 16.0 g of hydroxylamine hydrochloride are added and the mixture is refluxed for 2 hours. It is evaporated, the residue dissolved in aqueous ethanol and more water is added until the solution becomes cloudy and its pH is adjusted to about 7. On cooling, a precipitate slowly separates, which is collected and recrystallized from acetonitrile to yield the oxime of the 5-(p-fluorobenzylamino)-pyridine-2-carboxaldehyde melting at 167°–169°.

13.2 g thereof are dissolved in 130 ml of trifluoroacetic anhydride and the solution is stirred for 3½ hours. Thereupon, 400 ml of methanol are slowly added and the mixture is poured into aqueous sodium bicarbonate. It is extracted with ethyl acetate, the extract washed with water, dried and evaporated. 1.7 g of the resulting trifluoroacetyl oxime are dissolved in 15 ml of pyridine while stirring and 0.63 g of methanesulfonyl chloride are added. The mixture is stirred for 2 hours at room temperature and warmed on the steam bath for another 2 hours. It is evaporated and the residue dissolved in a mixture of cold water and diethyl ether. The aqueous solution is basified to pH=8–9 with sodium bicarbonate and extracted with ethyl acetate. The extract is washed with diluted aqueous sodium bicarbonate, hydrochloric acid and water, dried and evaporated. The residue is crystallized from acetonitrile-diethyl ether and recrystallized from methylcyclohexane, to yield the 5-(N-trifluoroacetyl-N-p-fluorobenzylamino)-pyridine-2-carboxylic acid nitrile melting at 119°–121°.

13.5 g thereof are dissolved in 90 ml of methanol and the solution mixed with 45 ml of 1 N aqueous sodium hydroxide. The mixture is warmed on the steam bath for 10 minutes, diluted with water and extracted with ethyl acetate-diethyl ether. The organic phase is washed with water, dried and evaporated. The residu oil is filtered through a silica gel column and eluted with 1,000 ml of chloroform-ethyl acetate (4:1). The eluate is evaporated and the residue crystallized from ethylacetate-diethyl ether, to yield the 5-(p-fluorobenzylamino)-pyridine-2-carboxylic acid nitrile melting at 88°–90°.

EXAMPLE 27

1.14 g of 5-(p-fluorobenzylamino)-pyridine-2-carboxylic acid nitrile are dissolved in 2.5 ml of dimethylformamide containing 0.358 g of sodium azide and 0.268 g of ammonium chloride. The mixture is heated on the steam bath 6 hours while stirring, cooled and diluted with water. The precipitate formed is collected and recrystallized from aqueous acetic acid, to yield the tetrazide of said acid, or the 2-(2H-tetrazolyl-5)-5-(p-fluorobenzylamino)-pyridine respectively, melting at 224°–227°.

EXAMPLE 28

2.0 g of 5-(p-fluorobenzylamino)-pyridine-2-carboxylic acid methyl ester are dissolved in 25 ml of methanol containing 1.28 g of hydrazine. The mixture is refluxed for 3 hours then cooled and diluted with a few ml of water. The solution is filtered the filtrate further diluted with water, to yield a crystalline solid, which is collected and washed with water, methanol and diethyl ether; it represents the 5-(p-fluorobenzylamino)-pyridine-2-carboxylic acid hydrazide melting at 153°–158°.

EXAMPLE 29

7.1 g 5-(p-fluorobenzylamino)-pyridine-2-carboxylic acid methyl ester are dissolved in 20 ml of isopropanol and 1.5 ml of 20 N aqueous sodium hydroxide are added. The solution is warmed for 15–20 minutes on the steam bath, then cooled in an ice bath. 5 ml of acetone are added while scratching, the crystalline solid formed is collected and washed with isopropanol and diethyl ether, to yield the sodium salt of the 5-(p-fluorobenzylamino)-pyridine-2-carboxylic acid melting at 275°–280° with decomposition.

EXAMPLE 30

3.06 g of 5-(p-fluorobenzylamino)-pyridine-2-carboxylic acid are suspended in 20 ml of water and 10 ml aqueous sodium hydroxide are added. The mixture is warmed until a clear solution is present, and 30 ml of hot water, containing 0.85 g calcium chloride are added. A bulky precipitate appears, but heating is continued for another ½ hour. The mixture is cooled, the solid collected and washed with hot water, ethanol and diethyl ether, to yield the neutral calcium salt of the 5-(p-fluorobenzylamino)-pyridine-2-carboxylic acid melting at 340° with decomposition.

EXAMPLE 31

The suspension of 40 g of 5-(N-carbomethoxy-N-p-fluorophenylethyl-1-amino)-pyridine-2-carboxylic acid methyl ester in 100 ml of water containing 30 ml of 20% aqueous potassium hydroxide is refluxed for 18 hours. On cooling, the potassium salt separates which is collected and redissolved in water. The solution is washed with diethyl ether, the aqueous layer acidified to pH=4–5 with hydrochloric acid, the precipitate collected and recrystallized from ethyl acetate-acetonitrile, to yield the 5-(p-fluorophenylethyl-1-amino)-pyridine-2-carboxylic acid melting at 214°–217°. Analogously, the 5-phenylethyl-1-amino-pyridine-2-carboxylic acid is obtained, melting at 213°–215°.

The starting material is prepared as follows: 27.6 g of 5-methoxycarbonylamino-pyridine-2-carboxylic acid methyl ester are added all at once to the suspension of 6.6 g of 50% sodium hydride in mineral oil and 400 ml of dimethylsulfoxide. The mixture is stirred at room temperature for 2½ hours and combined with the solution of 25 g of p-fluorophenylethyl-1 chloride in 50 ml of dimethylsulfoxide. The mixture is warmed to 70° for 18 hours and poured into 1 liter of water containing 15 ml of 12 N hydrochloric acid. It is extracted 4 times with 200 ml portions of diethyl ether, the extract washed with water, dried and evaporated, to yield the 5-(N-carbomethoxy-N-p-fluorophenylethyl-1-amino)-pyridine-2-carboxylic acid methyl ester as an oil.

EXAMPLE 32

According to the methods illustrated by the previous examples, the following compounds of the Formula

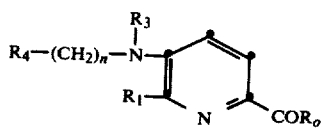

are prepared from equivalent amounts of the corresponding starting materials:

| No. | $R_o$ | $R_3$ | n | $R_4$ | $R_1$ | m.p. °C. |
|---|---|---|---|---|---|---|
| 1 | OCH$_3$ | H | 4 | H | H | 79–82 |
| 2 | OH | H | 2 | C$_6$H$_5$ | H | 65–70 |
| 3 | " | H | 1 | m-CH$_3$—C$_6$H$_4$ | H | 155–158 |
| 4 | " | CH$_3$ | 1 | " | H | 137–140 |
| 5 | " | H | 1 | p-(CH$_3$)$_3$C—C$_6$H$_4$ | H | 169–172 |
| 6 | " | CH$_3$ | 1 | m-CH$_3$O—C$_6$H$_4$ | H | 130–134 |
| 7 | " | H | 1 | " | H | 143–147 |
| 8 | ONa | H | 1 | o-F—C$_6$H$_4$ | H | 135 |
| 9 | OH | CH$_3$ | 1 | m-F—C$_6$H$_4$ | H | 151–156 |
| 10 | OCH$_3$ | " | 1 | m-Cl—C$_6$H$_4$ | H | 89–91 |
| 11 | OH | " | 1 | " | CH$_3$ | 85–90 |
| 12 | ONa | H | 1 | " | " | 240–245 |
| 13 | " | H | 1 | o-Cl—C$_6$H$_4$ | H | 245–250 |
| 14 | " | H | 1 | p-Cl—C$_6$H$_4$ | H | 293–296 |
| 15 | OCH$_3$ | H | 1 | p-Cl—C$_6$H$_4$ | H | 130–133 |
| 16 | OH | H | 1 | 3,4-Cl$_2$—C$_6$H$_3$ | H | 218–223 |
| 17 | ONa | H | 1 | " | H | 315–320 |
| 18 | " | H | 1 | m-Br—C$_6$H$_4$ | H | 245–250 |
| 19 | OH | CH$_3$ | 1 | " | H | 158–161 |
| 20 | " | H | 1 | m-CF$_3$—C$_6$H$_4$ | H | 214–217 |
| 21 | " | H | 1 | p-CF$_3$—C$_6$H$_4$ | H | 218–221 |
| 22 | " | H | 1 | p-H$_2$NCO—C$_6$H$_4$ | H | 258–261 |
| 23 | " | H | 1 | m-C$_6$H$_5$—O—C$_6$H$_4$ | H | 158–162 |
| 24 | " | CH$_3$ | 1 | " | H | 121–123 |
| 25 | " | H | 1 | m-F-p-CH$_3$O—C$_6$H$_3$ | H | 213–216 |
| 26 | " | H | 1 | 3,4,5-(CH$_3$O)$_3$—C$_6$H$_2$ | H | 224–227 |

EXAMPLE 33

Preparation of 10,000 tablets each containing 100 mg of the active ingredient:

| Formula: | |
|---|---|
| 5-(p-fluorobenzylamino)-pyridine-2-carboxylic acid | 1,000.00 g |
| Lactose | 2,535.00 g |
| Corn Starch | 125.00 g |
| Polyethylene glycol 6,000 | 150.00 g |
| Talcum powder | 150.00 g |
| Magnesium stearate | 40.00 g |
| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 65 ml of water and the suspension added to the boiling solution of the polyethylene glycol in 260 ml of water. The paste formed is added to the powders which are granulated, if necessary, with an additional amount of water. The granulate is dried overnight at 35°, broken on a screen with 1.2 mm openings and compressed into tablets using concave punches with 10.3 mm diameter, uppers bisected.

Analogously tablets are prepared, which contain one of the remaining compounds of the previous examples.

I claim:

1. A method of treating hypertension in mammals, which comprises administering to said mammals in need of such treatment enterally or parenterally a composition comprising a hypotensively effective amount of a compound of the formula

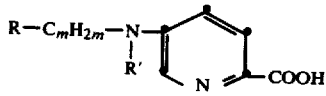

wherein R is hydrogen, phenyl, or phenyl substituted by up to two members selected from lower alkyl, lower alkoxy, halogeno, trifluoromethyl, cyano, carbamoyl or phenoxy, R' is hydrogen, lower alkyl or benzyl, m is an integer from 1 to 4, or a therapeutically acceptable ammonium, alkali metal or acid addition salt thereof, together with a pharmaceutical excipient.

2. A method as claimed in claim 1, wherein the 5-(p-fluorobenzylamino)-pyridine-2-carboxylic acid, or a therapeutically acceptable ammonium, alkali metal or acid addition salt thereof is administered.

3. A method as claimed in claim 1, wherein the 5-(m-chlorobenzylamino)-pyridine-2-carboxylic acid, or a therapeutically acceptable ammonium, alkali metal or acid addition salt thereof is administered.

* * * * *